United States Patent
Yilmaz et al.

(10) Patent No.: US 10,327,783 B2
(45) Date of Patent: Jun. 25, 2019

(54) ROBOTIC EMBOLISATION DEVICE AND SYSTEM

(71) Applicant: INVAMED SAGLIK iLAçSANAYi VE TiCARET A. S., Ankara (TR)

(72) Inventors: Muhammet Fatih Yilmaz, Ankara (TR); Cüneyt Köksoy, Ankara (TR); A. Kürsat Bozkurt, Istanbul (TR)

(73) Assignee: INVAMED SAGLIK ILAC SANAYI VE TICARET A.S., Ankara (TR)

( * ) Notice: Subject to any disclaimer, the term of this patent is extended or adjusted under 35 U.S.C. 154(b) by 271 days.

(21) Appl. No.: 15/464,274

(22) Filed: Mar. 20, 2017

(65) Prior Publication Data
US 2017/0265871 A1    Sep. 21, 2017

(30) Foreign Application Priority Data
Mar. 18, 2016    (TR) .............................. 2016/03535 U

(51) Int. Cl.
| | |
|---|---|
| *A61B 17/12* | (2006.01) |
| *A61B 34/32* | (2016.01) |
| *A61B 90/00* | (2016.01) |
| *A61B 34/00* | (2016.01) |
| *A61M 25/00* | (2006.01) |
| *A61B 17/00* | (2006.01) |
| *A61B 90/30* | (2016.01) |
| *A61B 34/30* | (2016.01) |

(52) U.S. Cl.
CPC .. *A61B 17/12181* (2013.01); *A61B 17/00491* (2013.01); *A61B 17/12109* (2013.01); *A61B 17/12113* (2013.01); *A61B 17/12195* (2013.01); *A61B 34/30* (2016.02); *A61B 34/32* (2016.02); *A61B 34/71* (2016.02); *A61B 90/30* (2016.02); *A61B 90/39* (2016.02); *A61M 25/0026* (2013.01); *A61B 2017/005* (2013.01); *A61B 2017/00398* (2013.01); *A61B 2017/00477* (2013.01); *A61B 2017/12054* (2013.01); *A61B 2034/301* (2016.02); *A61B 2034/303* (2016.02); *A61B 2090/306* (2016.02); *A61M 25/00* (2013.01); *A61M 2025/0008* (2013.01)

(58) Field of Classification Search
CPC ........ A61B 17/00491; A61B 17/12022; A61B 17/12027; A61B 17/12031; A61B 17/12036; A61B 17/12109; A61B 17/12113; A61B 17/12186; A61B 2017/005; A61B 2017/00504; A61B 2017/00508; A61B 2017/00778
See application file for complete search history.

(56) References Cited

U.S. PATENT DOCUMENTS

| | | | | |
|---|---|---|---|---|
| 2010/0280312 | A1* | 11/2010 | D'Alessio | ........ A61B 17/00491 600/104 |
| 2011/0152759 | A1* | 6/2011 | Clymer | .............. A61B 10/0283 604/93.01 |
| 2013/0211374 | A1* | 8/2013 | Hetherington | ..... A61B 17/8822 604/506 |
| 2014/0088553 | A1* | 3/2014 | Hetherington | ..... A61B 17/8822 604/506 |

\* cited by examiner

*Primary Examiner* — Todd J Scherbel
(74) *Attorney, Agent, or Firm* — Gokalp Bayramoglu

(57) ABSTRACT

The invention has been particularly developed for a controlled embolisation application in arterial and venous embolisation, and relates to a device used for halting the progression of aneurysm and reflux closing/aneurysms, blocking/arteries closing/arteriovenous malformations/-venous reflux procedures.

10 Claims, 6 Drawing Sheets

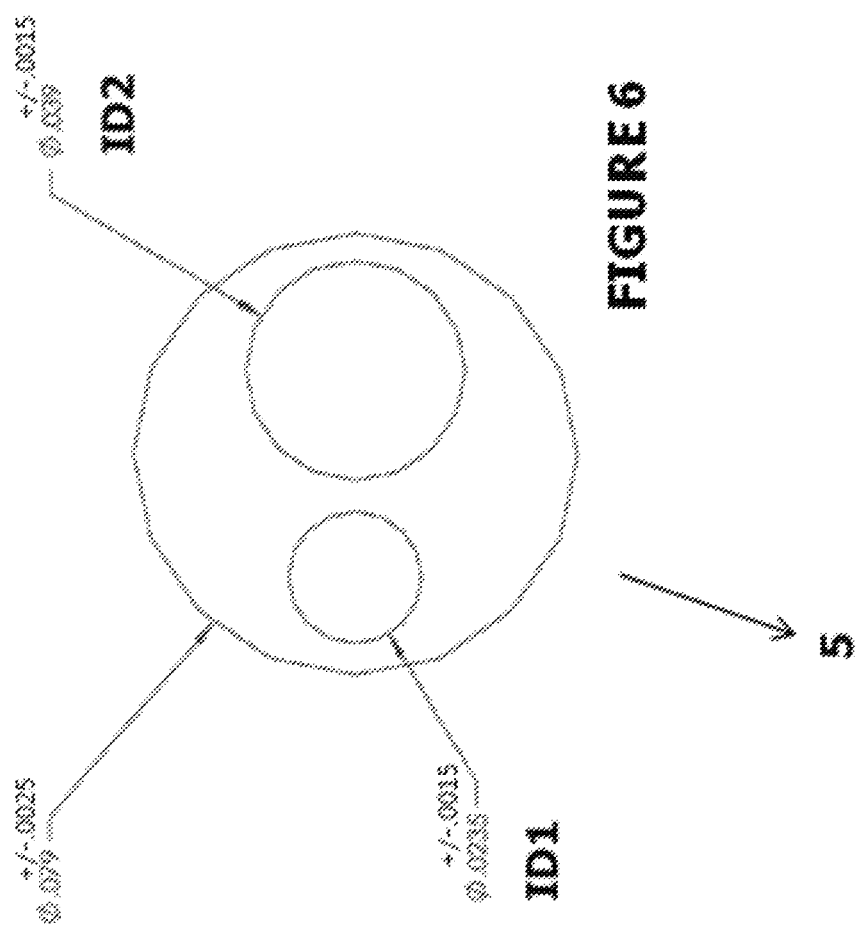

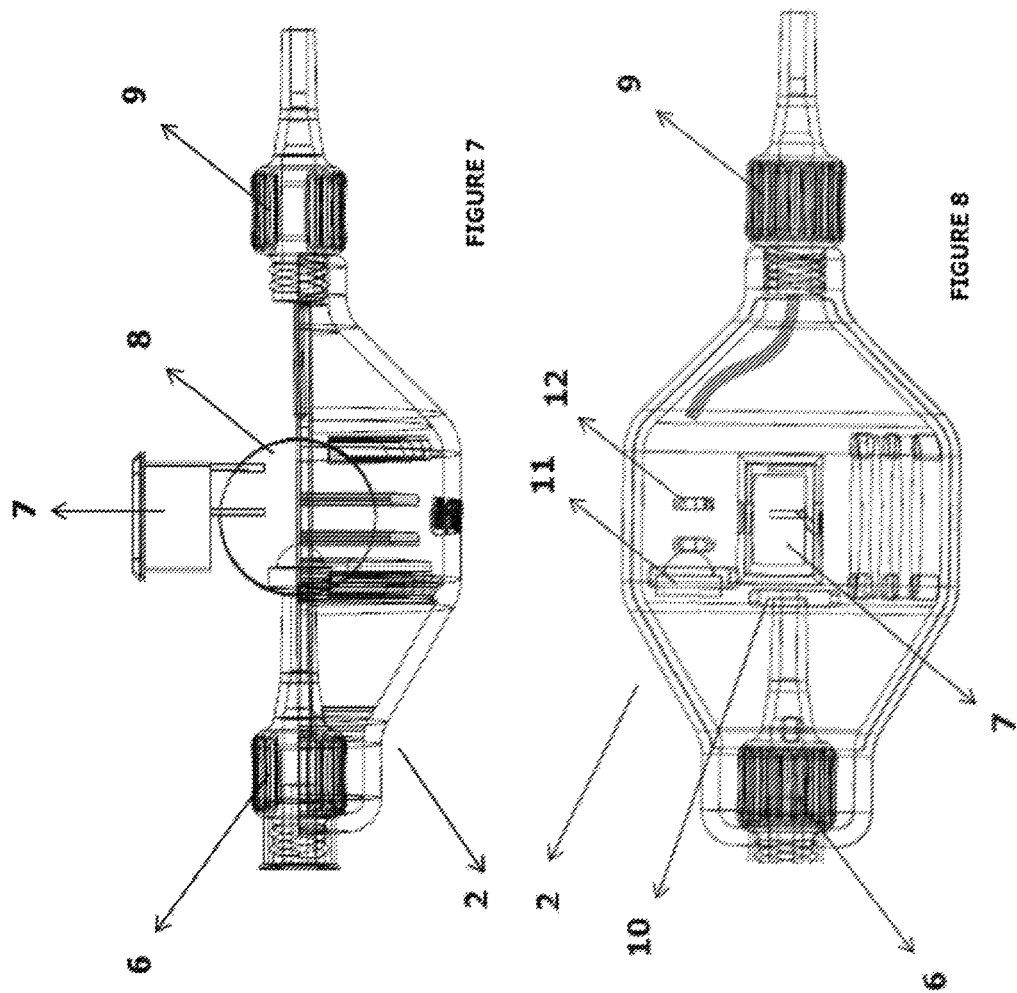

ROBOTIC EMBOLISATION DEVICE AND SYSTEM

CROSS REFERENCE TO RELATED APPLICATIONS

This application claims priority to Turkish Application No. TR 2016/03535, filed on Mar. 18, 2016, the entire contents of which are incorporated herein by reference.

TECHNICAL FIELD

The invention has been particularly developed for a controlled embolisation application in arterial and venous embolisation, and relates to a device used for halting the progression of aneurysm or reflux /closing aneurysms/ blocking arteries/closing arteriovenous malformations/venous reflux procedures.

BACKGROUND OF THE INVENTION

The studies conducted in the state of the art showed that the embolisation system is completely dependent on human skills and is performed, manually. The most significant problem in the embolisation procedure for the patients includes both the deviations in dose adjustment and the variation in catheter withdrawal speed from one person to another due to the manual nature of the dose determination depending on the vessel diameter of the respective embolisation site and the catheter withdrawal speed.

The problems of dosage and catheter withdrawal speed are experienced in the embolic agent systems administered with an injector or a gun. An even distribution of the agent to every part of the vessel cannot be achieved in a manual system. This, in turn, results in a denser embolic agent delivery in some parts, while a more sparse delivery in the others. As a consequence, the areas with dense embolic agent delivery develop thrombophlebitis, induration, rash, and temperature increase. In the areas with sparse embolic agent delivery, on the other hand, a sufficient and proper sealing cannot be achieved, and so the procedure fails and the standardization of the procedure cannot be performed.

SUMMARY OF THE INVENTION

It is aimed by the device and system according to the invention to block/close varicose veins in fibrosis after the adhesion lumen, without requiring anesthesia (an approximately diluted local, anesthetic large volume infusion and along the entire length of the vein). Thus, post-surgical compression application will be needed less.

BRIEF DESCRIPTION OF THE DRAWINGS

The drawings illustrating the robotic embolisation device and system developed with the present invention are given below for a better understanding of the invention.

FIG. 6 is a cross-sectional view of the double-lumen catheter.

FIG. 7 is a side interior view of the light source adapter.

FIG. 8 is a top interior view of the light source adapter.

DEFINITION OF THE ASPECTS/SECTIONS/PARTS FORMING THE INVENTION

Figure 1:
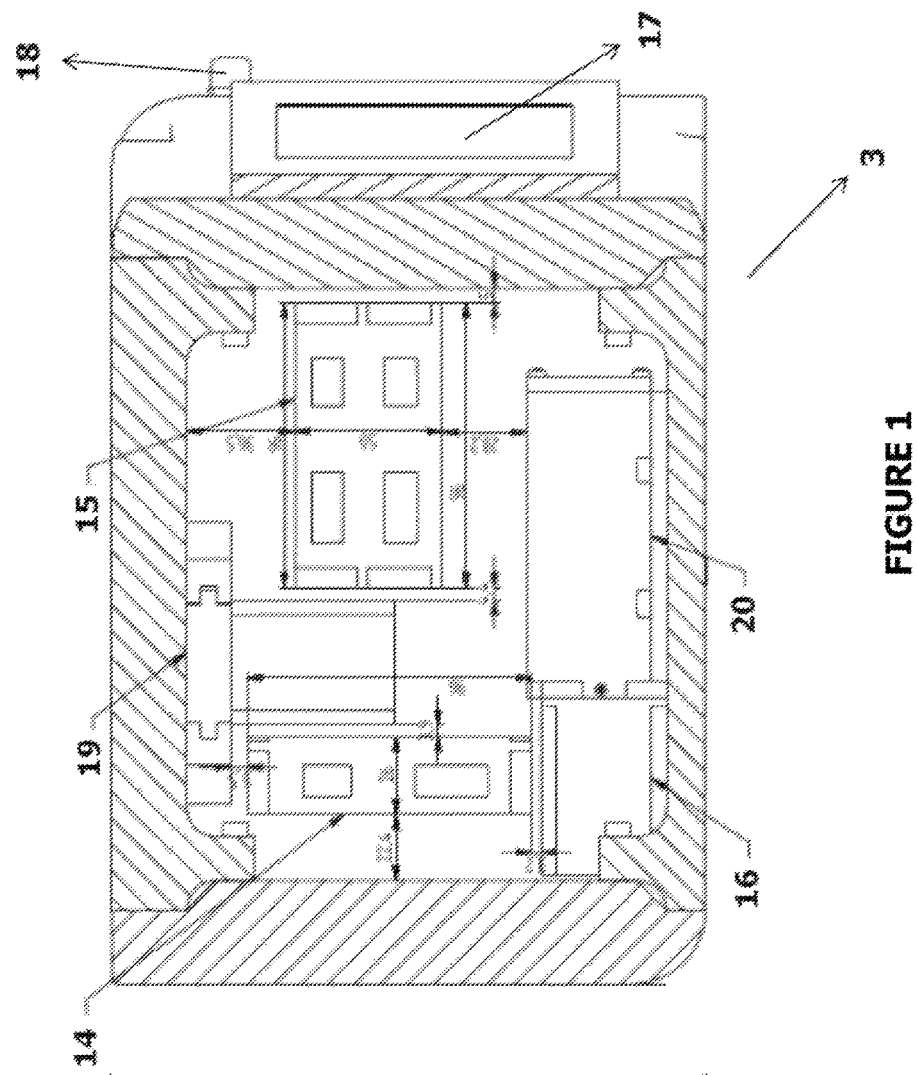
FIG. 1 is a cross-sectional view of the robotic embolisation device.
Figure 2:
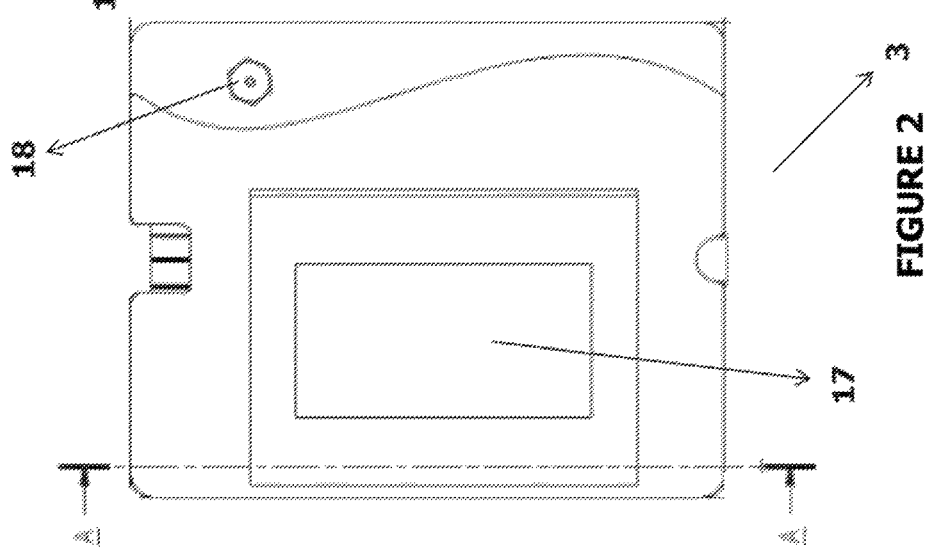
FIG. 2 is a front panel view of the robotic embolisation device.
Figure 3:
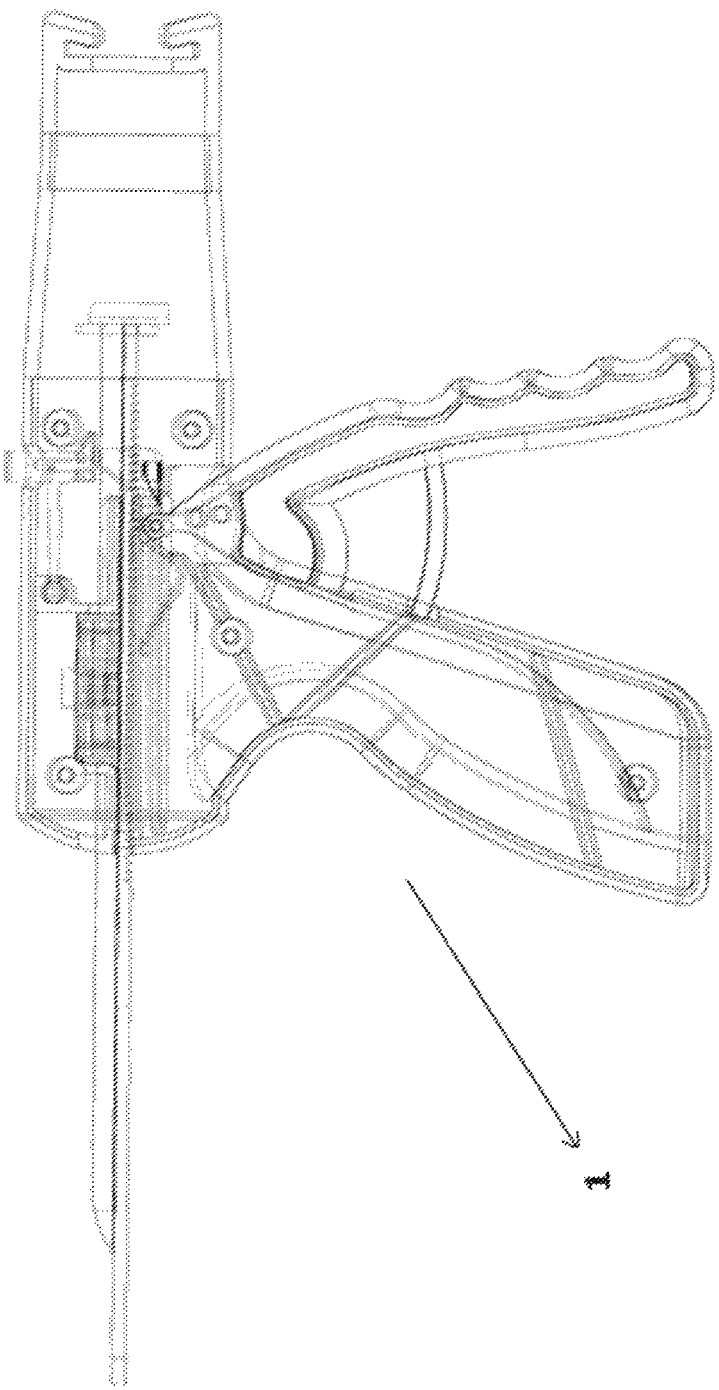
FIG. 3 is an interior view of the injection gun of the prior art.
Figure 4:
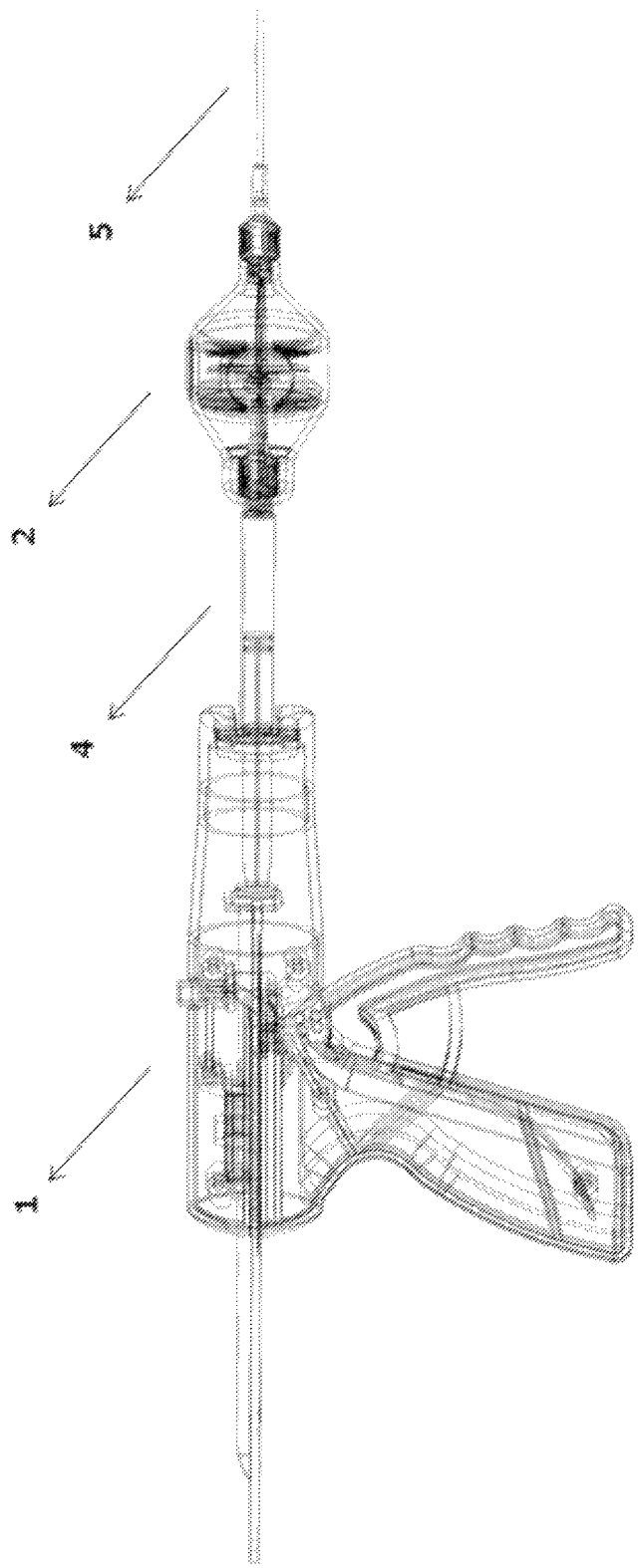
FIG. 4 is an interior view of the embolisation system comprising the injection gun when the gun injector, light source adapter, and double-lumen catheter are mounted thereon.
Figure 5:
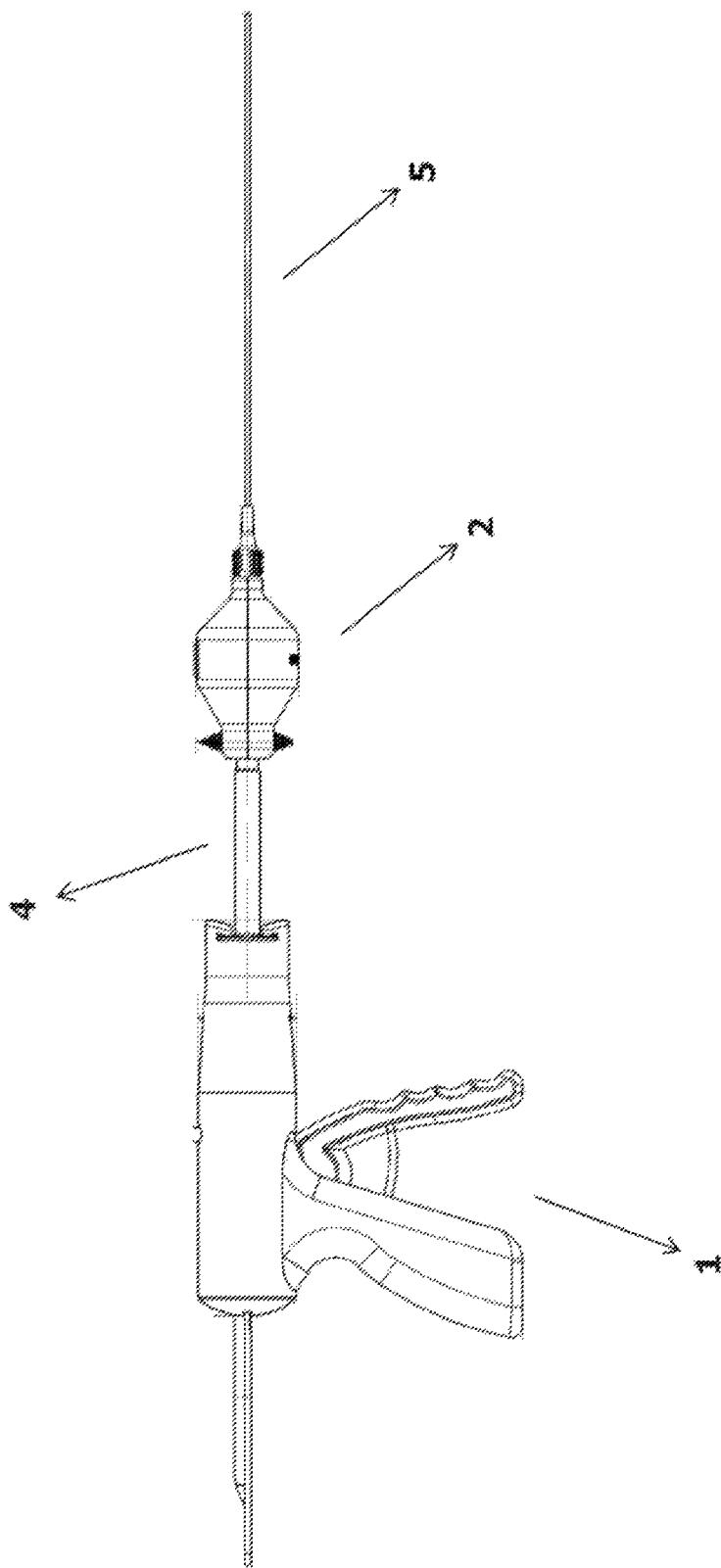
FIG. 5 is an overall view of the embolisation system comprising the injection gun when the gun injector, light source adapter, and double-lumen catheter are mounted thereon.

The parts/portions/components which are shown in the drawings illustrating the robotic embolisation device and system developed with the present invention for a better understanding of the invention are enumerated individually and the reference numbers corresponding thereto are given below.

1. Injection gun (prior art)
2. Light source adapter
3. Robotic embolisation device
4. Gun injector
5. Double-lumen catheter
6. Injector connection port
7. On/off switch
8. Power supply battery
9. Catheter connection port
10. SS (stainless steel) pin
11. Light source
12. Fiber retaining pin
14. PLC unit
15. Motor driver
16. Drive motor (Step motor)
17. PLC control display
18. Fiber connection input
19. Bobbin mechanism
20. Robotic embolisation device injector
ID1: Small lumen
ID2: Large lumen

DETAILED DESCRIPTION OF THE INVENTION

In the systems where the device according to the invention is used, the procedure is performed with local anesthesia. During the procedure, an introducer sheath is placed into the distal great saphenous vein of the affected leg with ultrasound and a delivery catheter (5) is immediately advanced to the pre-saphenofemoral position, and then the proximal vein is compressed and a calibrated dose of cyanoacrylate adhesive is delivered manually by means of the injector (4) or gun (1) through the tip of catheter (5) by the operating surgeon for sealing the vein. Afterwards, the catheter (5) is removed in step-wise manner and the progress is monitored with repeated steps (i.e. proximal venous compression and a more calibrated dose) for blocking the vein using ultrasound imaging. Moreover, the procedure may be similarly performed for the small saphenous vein.

The embolisation materials administered via surgical technique or by means of a gun (1) have varying viscosities. Therefore, a robotic device has been developed for a continuous catheter (5) withdrawal.

Regardless of the embolisation material (ethyl-methyl-octyl-nbutyl cyanoacrylate/DMSO-ethylenevinylalcohol/PVA/aethoxysklerol), an accurate dosing allows the embolisation to be a correct administration option.

An excess of embolic agent typically causes inflammation, phlebitis, hyperemia, DVT, etc, particularly in peripheral, areas. Unless administered sufficiently, the embolisation will not be fulfilled.

A light-guide embolisation catheter, however, allows for confirming the procedure. This type of catheter is a unique example around the world. The light guide shows the segment of the vein when the embolisation procedure is initiated. Applying compression to the proximal of the light guide not only promotes the polymerization but also prevents loss of time. Further, since the light guide produces light energy at 510 nm wavelength, this effect promotes the polymerization and at the same time cures.

Especially in the case of varicose vein treatment, the lack of a light guide in all of the systems but the invention reduces the margin of confirmation.

Laser light guide both give laser energy and at the same time measures the vessel diameter thanks to its sensors.

The amount of the embolic agent to be administered logarithmically to the measured vessel is calculated by the device.

Having administered the embolic agent at a predetermined amount, the catheter (5) starts to withdraw automatically, thereby ensuring optimum embolisation in direct proportion.

Administering a dose suitable for different vessel diameters may also allow an efficient administration to the vessel with an aneurysmatic expansion segment.

The robotic embolisation device and system according to the invention basically has 2 (two) main components. One of them is the robotic embolisation device (3) which allows performing the embolisation procedure in a complete robotized fashion, and the other is the embolisation system which ensures that the embolisation procedure is conducted with minimum error and maximum efficiency by being mounted, in the present robotic embolisation device (3), or in the injection gun (1) of the prior art, the embolisation system comprising a light source adapter (2), a gun injector (4), and a double-lumen catheter (5).

1. Robotic embolisation device (3):
    It is the component of the system which provides controlling the drive motors (16) at the desired values, switching on/off, and also controlling the laser, wherein the following are comprised:
        At least one terminal transferring the energy from the power supply to the system,
        At least one PLC unit (14) which is commanded over the PLC control display (17) and where the automation software is installed,
        At least one motor driver (15) by which the angular sensitivity of the drive motor (16) during use is adjusted,
        At least one drive motor (16) which allows 3-phase and 1.2 step control, the drive motor controlling the bobbins (19) and the injector (20) at suitable pulse values within the system,
        At least one PLC control display (17) through which the PLC unit (14) is commanded,
        At least one fiber connection input (18) which transmits light to the fiber by means of the one light source comprised thereon,
        At least one bobbin mechanism (19), and
        At least one robotic embolisation device (20).
    The drive motor (16) here is a step motor.
2. Injection gun (1): It is the component which delivers the gun injector (4) at standard doses with each shot,
3. Injector (4 and 20): Its volume is 2 cc in the injection gun (1) system while 5 cc in the robotic embolisation device and it is the component which stores the polymer and transfers into the catheter (5).
4. Light source adapter (2): It is the component which supplies light to the fiber optic cable by means of the light source (11) and which creates a light at the tip of the catheter (5), wherein it has channels for advancing the polymer into the catheter (5) and comprises:
    At least one injector connection port (6) through which the gun injector (4) is connected, an SS pin (10) being connected to the other end thereof,
    An on/off switch (7) through which the light source (11) is switched on and off,
    At least one 12V power supply battery,
    At least one catheter connection port (9) through which the catheter (5) is connected to the adapter (2),
    An SS pin (10) for interconnecting the catheter and (5) and the injector connection port (6),
    At least one light source (11) for supplying light to the fiber optic cable, and
    At least one fiber retaining pin (12) which enables the fiber optic cable to be positioned at the focal point of the light source (11),
    The light source (11) is a red light source having a wavelength of 510 mm.
    The SS pin (10) is made of stainless steel and has the dimensions given below:
        SS 304,
        Outer Diameter (OD): 0.7 mm,
        Inner diameter (ID): 0.5 mm, and
        Length: 60 mm.
5. Double-lumen catheter (5): Its raw material is polytetrafluoroethylene (PTFE) and it has two lumens. (OD: 2 mm, ID1: 0.6 mm, ID2: 1 mm). A fiber optic cable, for transmitting light, passes through the ID2. And polymer is advanced through the ID1. The end portion is rounded and directly advances through the vein. It is provided thereon with a sheath made of PE (polyethylene) having markers at each cm.

What is claimed is:

1. A robotic embolisation apparatus developed for a controlled embolisation application in arterial and venous embolization, comprising a robotic embolization device and an embolization system,
    wherein the robotic embolisation apparatus is used for halting a progression of aneurysm or reflux/closing aneurysms/blocking arteries/closing arteriovenous malformations/venous reflux procedures,
    wherein the robotic embolisation device for controlling a laser within the embolisation system comprises:
    at least one terminal transferring energy from a power supply to the embolisation system,
    at least one PLC unit which is commanded over a PLC control display and where an automation software is installed,
    a drive motor which allows 3-phase and 1.2 step control, the drive motor controlling bobbins and a device injector at suitable pulse values within the embolisation system, wherein the robotic embolization device controls the drive motor at desired values,
    at least one motor driver by which an angular sensitivity of the drive motor during use is adjusted,
    the at least one PLC control display through which the PLC unit is commanded,
    at least one fiber connection input which transmits light to fiber by means of a light source comprised thereon, at least one bobbin mechanism, and
at least one robotic embolisation means;
wherein the robotic embolisation apparatus further comprises an injection gun comprising a gun injector;
wherein the embolization system comprises:
the gun injector whose volume is 2 cc in an injection gun system while 5 cc in the robotic embolisation device, and which stores a polymer and transfers the polymer into a catheter;
a light source adapter which supplies light to a fiber optic cable by means of the light source and which creates a light at a tip of the catheter, wherein the light source adapter has channels for advancing the polymer into the catheter and comprises:
at least one injector connection port the gun injector being connected to one end of the injector connection port, a stainless steel pin (SS pin) being connected to an other end of the injector connection port,
an on/off switch through which the light source is switched on and off, wherein the robotic embolization device controls the on/off switch,
at least one 12V power supply battery,
at least one catheter connection port through which the catheter is connected to the light source adapter,
the SS pin for interconnecting the catheter and the injector connection port,
the light source for supplying the light to the fiber optic cable, and
at least one fiber retaining pin which enables the fiber optic cable to be positioned at a focal point of the light source; and
the catheter with an inner diameter 1 (ID1) lumen and an inner diameter 2 (ID2) lumen, an end portion of which is rounded in form and which is capable of advancing through a vein, wherein the catheter is provided thereon with a polyethylene (PE) sheath having markers at each cm.

2. The robotic embolisation apparatus according to claim 1, wherein the drive motor is a step motor.

3. The robotic embolisation apparatus according to claim 1, wherein the light source is a red light source having a wavelength of 510 nm.

4. The robotic embolisation apparatus according to claim 1, wherein dimensions of the SS pin are as follows:
SS 304,
an outer diameter (OD): 0.7 mm,
an inner diameter (ID): 0.5 mm, and
a length: 60 mm.

5. The robotic embolisation apparatus according to claim 1, wherein a raw material of the catheter is PTFE.

6. The robotic embolisation apparatus according to claim 1, wherein an outer diameter (OD) of the catheter is 2 mm.

7. The robotic embolisation apparatus according to claim 1, wherein the ID1 lumen is 0.6 mm in diameter.

8. The robotic embolisation apparatus according to claim 1, wherein the ID2 lumen is 1 mm in diameter.

9. The robotic embolisation apparatus according to claim 1, wherein the ID1 lumen has a form allowing a delivery of the polymer therethrough.

10. The robotic embolisation apparatus according to claim 1, wherein the ID2 lumen has a form allowing a passage of the fiber optic cable therethrough.

* * * * *

UNITED STATES PATENT AND TRADEMARK OFFICE
CERTIFICATE OF CORRECTION

PATENT NO. : 10,327,783 B2
APPLICATION NO. : 15/464274
DATED : June 25, 2019
INVENTOR(S) : Yilmaz et al.

Page 1 of 1

It is certified that error appears in the above-identified patent and that said Letters Patent is hereby corrected as shown below:

On the Title Page

Item (72), The INVENTOR(S) should read MUHAMMET FATiH YILMAZ; CÜNEYT KÖKSOY; A. KÜRSAT BOZKURT; RASIT DINC Signed and Sealed this
Eleventh Day of August, 2020

Andrei Iancu
*Director of the United States Patent and Trademark Office*